(12) United States Patent  (10) Patent No.: US 8,328,570 B2
Sauter et al.  (45) Date of Patent: Dec. 11, 2012

(54) CONNECTOR FOR COUPLING A HANDPIECE TO A DENTAL TREATMENT CENTER

(75) Inventors: Johannes Sauter, Mittelbuch (DE); Richard Buerk, Alberweiler (DE)

(73) Assignee: Kaltenbach & Voigt GmbH, Biberach (DE)

( * ) Notice: Subject to any disclaimer, the term of this patent is extended or adjusted under 35 U.S.C. 154(b) by 43 days.

(21) Appl. No.: 13/101,616

(22) Filed: May 5, 2011

(65) Prior Publication Data

US 2011/0207353 A1  Aug. 25, 2011

Related U.S. Application Data

(62) Division of application No. 12/347,546, filed on Dec. 31, 2008.

(30) Foreign Application Priority Data

Feb. 18, 2008 (DE) .......................... 10 2008 009 623

(51) Int. Cl.
 *H01R 4/60* (2006.01)
(52) U.S. Cl. ........................................ 439/191; 439/126
(58) Field of Classification Search ............... 433/29, 433/126, 141; 439/192, 345, 191, 195, 700, 439/126, 955
See application file for complete search history.

(56) References Cited

U.S. PATENT DOCUMENTS 2,634,311 A * 4/1953 Darling .......................... 439/191
(Continued)

FOREIGN PATENT DOCUMENTS

AT  389 633 T  4/2008
(Continued)

OTHER PUBLICATIONS

English-language translation of International Preliminary Report on Patentability for Application No. PCT/EP2007/009462, dated May 5, 2009.

(Continued)

*Primary Examiner* — Phuong Dinh
(74) *Attorney, Agent, or Firm* — Marshall, Gerstein & Borun LLP

(57) ABSTRACT

A system for driving an electric handpiece in response to a pneumatic control signal may provide for fast interchange of handpieces, self-calibration and wide dynamic range of operation with precise speed control. The system may be incorporated into virtually any dental treatment center using traditional pneumatic drive handpieces, and a conversion kit may facilitate such conversion. The system may provide not only for controlling the speed and torque of a tool coupled to an electric drive handpiece responsive to a pneumatic control signal, it may also provide for coupling cooling air and treatment media, such as air and/or water to the handpiece. Coupling of a handpiece to an operating base of the system, including coupling of media lines and electrical connections may be made with a simple press and twist action using quick connection structure.

5 Claims, 6 Drawing Sheets

U.S. PATENT DOCUMENTS

| | | | |
|---|---|---|---|
| 4,900,252 A | | 2/1990 | Liefke et al. |
| 5,017,136 A | * | 5/1991 | Gatti ............................... 433/98 |
| 5,405,269 A | * | 4/1995 | Stupecky ...................... 439/191 |
| 5,501,596 A | | 3/1996 | Bailey |
| 5,947,729 A | * | 9/1999 | Bell ............................... 433/98 |
| 6,139,003 A | * | 10/2000 | Michalik et al. ........... 270/52.17 |
| 6,159,004 A | * | 12/2000 | Rosenstatter ................... 433/29 |
| 7,615,664 B2 | | 11/2009 | Herold et al. |
| 7,914,315 B2 | * | 3/2011 | Kuhn et al. ................... 439/345 |
| 2001/0031442 A1 | | 10/2001 | Mosimann |
| 2002/0127512 A1 | * | 9/2002 | Chen et al. ................... 433/119 |
| 2004/0166464 A1 | | 8/2004 | Schneider |

FOREIGN PATENT DOCUMENTS

| | | |
|---|---|---|
| FR | 2 584 918 A3 | 1/1987 |
| FR | 2 592 299 A1 | 7/1987 |

OTHER PUBLICATIONS

English-language translation of International Search Report and Written Opinion for Application No. PCT/EP2007/009462, dated Feb. 26, 2008.

* cited by examiner

CONNECTOR FOR COUPLING A HANDPIECE TO A DENTAL TREATMENT CENTER

CROSS-REFERENCE TO RELATED APPLICATIONS

This is a division of U.S. application Ser. No. 12/347,546 filed Dec. 31, 2008, which claims the priority benefit under USC 119 of DE 10 2008 009 623 filed Feb. 18, 2008, the entire respective disclosures of which are incorporated herein by reference.

TECHNICAL FIELD

This patent relates to the field of dental treatment, and in particular, this patent relates to a treatment center with an electric drive that is responsive to a pneumatic control signal.

BACKGROUND

Dental treatment centers have generally relied upon a controlled source of compressed air to drive air motor or turbine powered handpieces to effect treatment. Control of the speed of the handpiece is related to the pressure of the air reaching the air motor or turbine, and the air pressure is controlled by a pedal or similar device. Manipulation of the pedal allowed the practitioner to control very precisely the turbine speed and therefore the speed of rotation or oscillation of the tool mounted in the handpiece.

More recently, electric drive handpieces including compact electric motors that provide driving torque to the tool have found favor owing to their flexibility in controlling both the speed of operation as well as the torque exerted by the tool. However, most existing dental treatment center installations are configured for pneumatic handpieces and pneumatic control thereof. Generally speaking, replacement of the entire treatment center to support electric drive handpieces is cost prohibitive.

With the introduction of the ELECTROtorque TLC and the ELECTROtorque Plus systems, the assignee of the instant application offered a system providing pneumatic control of an electric drive for a handpiece. These devices tailored to the older dental treatment facility having only compressed air available as a drive medium, opened up the possibility of expanding the types of drive instruments that could be used with a treatment center. These devices operated by converting the compressed air previously used to drive the air motor or turbine into an electric control signal for driving an electric motor for operating the handpiece.

A device, such as the ELECTROtorque TLC or ELECTROtorque Plus, that converts the compressed air into a control signal must operate with a variety of treatment centers and with a variety of air supply conditions and pressures. To account for variations in air supply conditions, these systems and those like them require a calibration process to associate a maximum electric motor speed with a maximum system pressure of the treatment unit. The calibration process must be performed frequently and requires a number of specific and carefully planned steps taking time and effort.

Not only providing an electric control signal to the handpiece, the device converting the system air pressure to an electric control signal also provides cooling air to the handpiece and air and water media used in the treatment process. The system also needs to be flexible in accepting multiple different handpieces used in various procedures. Changing from one handpiece to another must be quick and easy and cannot require complicated changing over of medium line connections or complicated coupling of the electric motor to the handpiece. Generally, the initial setup, configuration, reconfiguration and use of the system should be simple and not require special training or procedures.

DETAILED DESCRIPTION

A system in accordance with the inventions of this patent for driving an electric handpiece in response to an operator controlled pneumatic control signal provides for fast interchange of handpieces, self-calibration and wide dynamic range of operation with precise speed control. The system may be incorporated into virtually any dental treatment center using traditional pneumatic drive handpieces, and a conversion kit facilitates such conversion. The system provides not only for controlling the speed and torque of a tool coupled to an electric drive handpiece responsive to a pneumatic control signal, it also provides for coupling the compressed air source for cooling and treatment media, such as air and/or water to the handpiece.

Coupling of a handpiece to an operating base of the system, including coupling of media lines and electrical connections may be made with a simple press and twist action. There is no requirement separately to couple media lines or electrical connections.

Automatic, self-calibration occurring upon initial use and continuously during use ensures a desired maximum tool speed always can be obtained and maintained regardless of fluctuations or changes in supply air pressure. Eliminated are the time consuming and complicated calibration procedures used in the prior art. Tool speed control over the full range of available air pressure provides precise speed control and enhanced feel, especially at the lowest and highest tool speeds.

Figure 1:
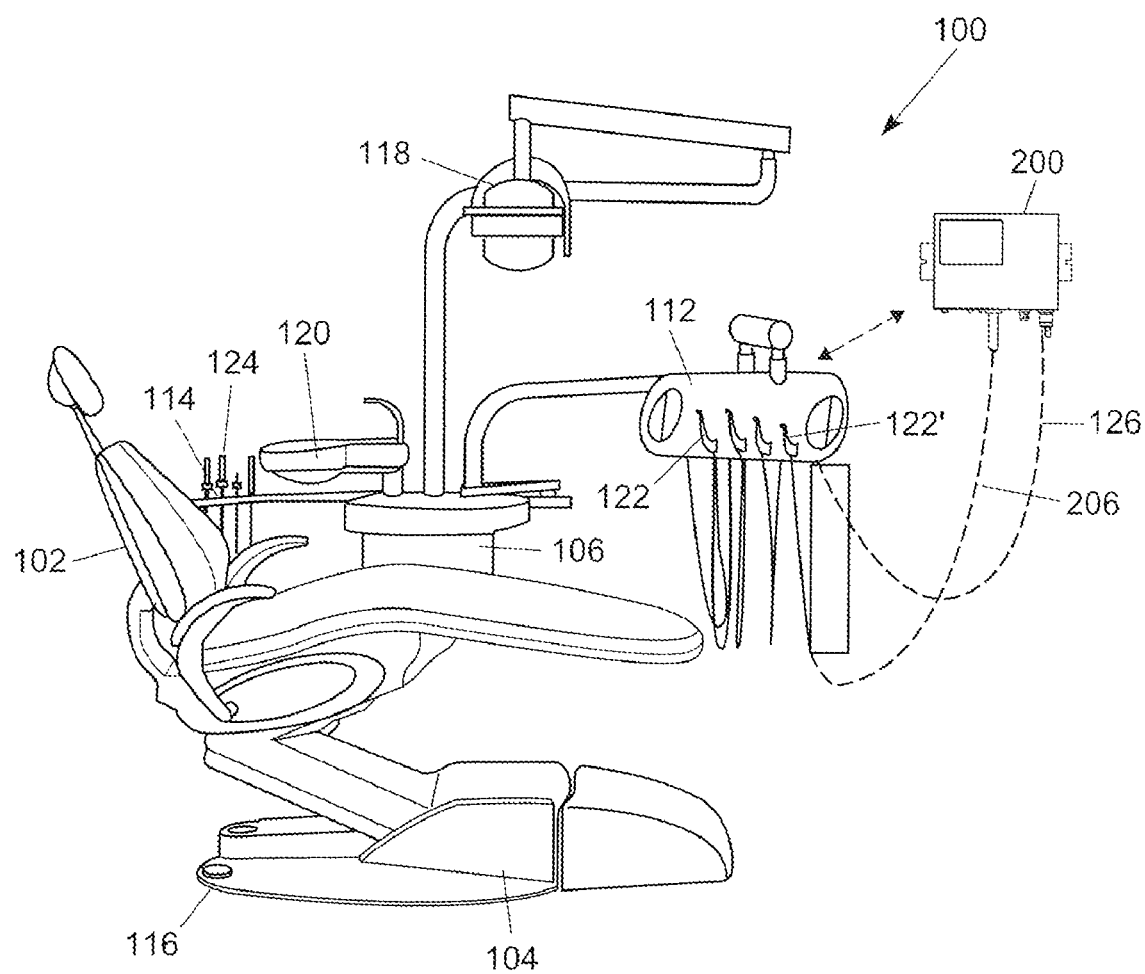
FIG. 1 is a graphic illustration of a dental treatment center incorporating a driving system in accordance with the embodiments of the invention.

FIG. 1 illustrates a dental treatment center 100 that includes a patient chair 102 mounted to an adjusting pedestal stand 104. A facilities base 106 provides a single mounting position for one or more treatment units, with two being illustrated a doctor delivery unit 112 and an assistant instrumentation unit 114. The treatment units may be operated from a foot actuated pedal 116 disposed within the pedestal stand 104. More than one pedal 116 may be provided, and two are shown in FIG. 1. A treatment light 118 and a cuspidor 120 may also be provided from the facilities base 106.

Each treatment unit may include one or more handpieces. For example, the doctor delivery unit 112 is configured for six (6) handpieces 122 while the assistant instrument unit 114 is configured for four (4) handpieces 124. Each handpiece is received within a slot (not visible) in the respective treatment unit 112/114.

The treatment center 100 may be coupled to sources (not depicted) of compressed air and treatment media such as water and air. Each handpiece may be a pneumatically operated handpiece. That is, each handpiece may operate based upon control of a supply of compressed air to the handpiece via the pedal 116. However, it may be desirable to utilize electric drive handpieces in the treatment center 100. This can be accomplished even where the treatment center 100 is solely configured as a pneumatic treatment center, i.e., capable only of providing compressed air as a drive source for the handpieces.

Upgrading the pneumatic powered treatment center 100 to electrical handpiece operation is effected by system 200 capable of converting the pneumatic signal from the pedal 116 that would otherwise directly drive a pneumatic handpiece into an electric signal to drive an electric handpiece. In this regard, the treatment center 100 capable only of accommodating pneumatic handpieces may be configured with one or more electric drive handpieces. One such electric drive handpiece is illustrated in FIG. 1 as handpiece 122', which may be a compact, micro-motor handpiece responsive to an electric drive signal, incorporates fiber optic work lighting, air cooling and media delivery. The system 200 may be fitted to the doctor delivery unit 112, the facilities base 106 or any other suitable location on the dental treatment center 100. The system 200 is then coupled to the dental treatment center 100 source of compressed air and treatment media via suitable line connections 126 and to the at least one handpiece 122'.

Figure 2:
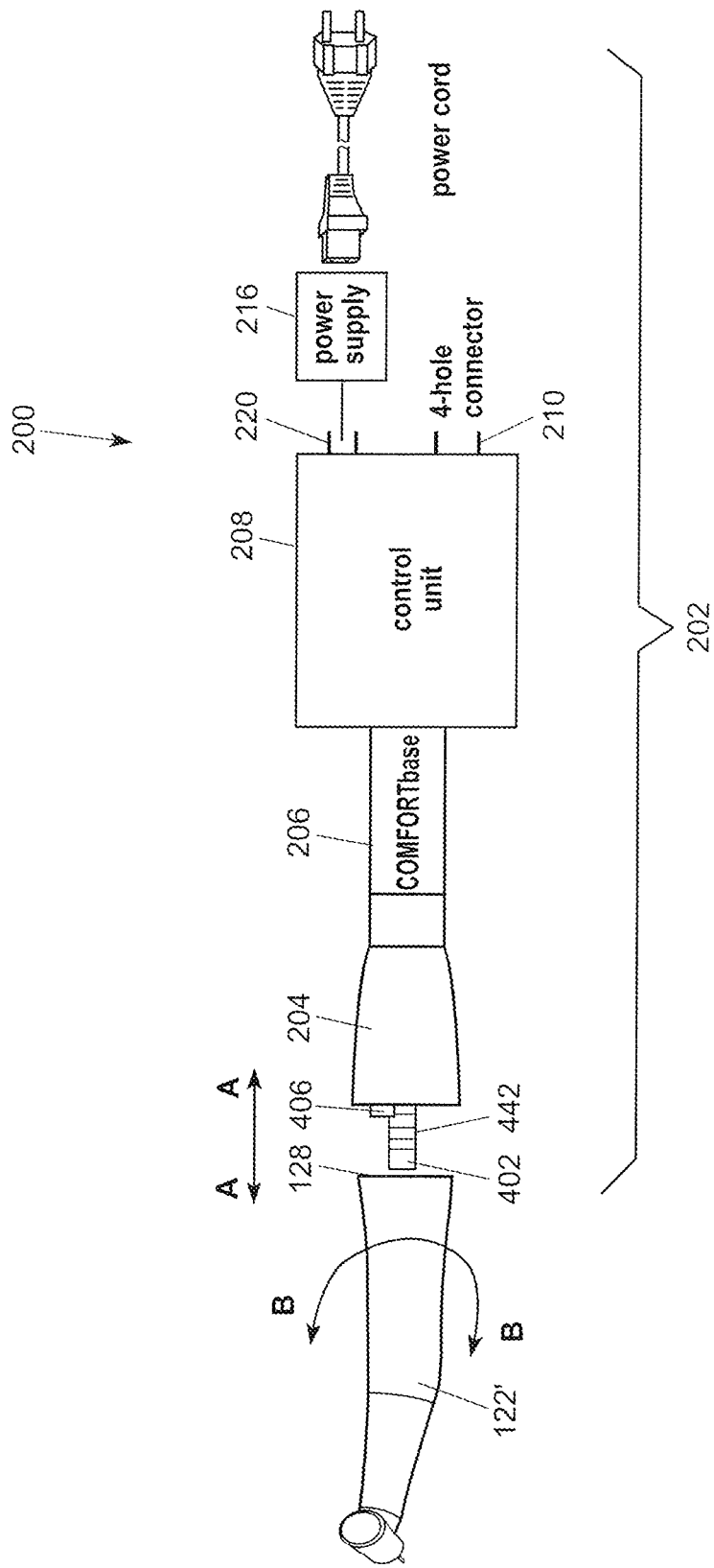
FIG. 2 is a schematic illustration of a system in accordance with embodiments of the invention.

FIG. 2 illustrates the system 200 for driving an electric handpiece 122' responsive to a pneumatic control signal in accordance with an embodiment of the invention. The system 200 may be used to adapt a pneumatic only treatment center and to utilize the pneumatic output of the control pedal 116 to provide a control signal to a drive an electric drive handpiece, such as the handpiece 122'.

The system 200 may be considered in two portions, a base or system portion 202 and an electric drive handpiece, such as the handpiece 122'. As will be explained, numerous handpieces having various configurations may be quickly and easily coupled to the base 202 via the quick connector 204. From the quick connector 204, a media and electrical coupling line 206 extends between the quick connector 204 and a control unit 208 thus coupling the electric drive handpiece 122' to the control unit 208 via the quick connector 204 and the line 206.

Figure 3:
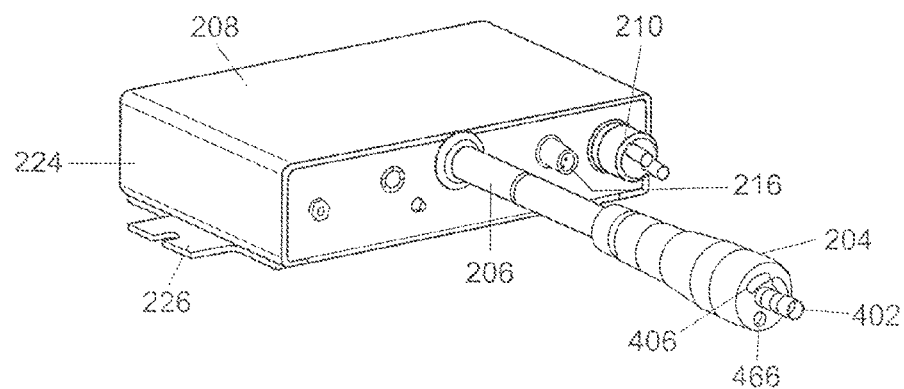
FIG. 3 is a schematic view of a control unit and associated connection of the system illustrated in FIG. 2.

The control unit 208 includes a plurality of media ports as part of a media connector 210 best seen in FIG. 3. The media connector 210 allows the control unit 208 to couple to a source of compressed air and treatment media such as air and water. Power is supplied from a main power source via a common or typical power cord 216 to provide power to the control unit 208 via the power-in port 220. A power supply within the control unit converts the available electrical power, e.g., 100 to 240 VAC; 47 to 60 Hz electrical power to 36 VDC for powering the control unit 208.

Referring in particular to FIG. 3, the media connector 210 may be formed as a four-port connector. The four-port connector is standard in the dental instrument industrial to allow coupling of the compressed air source (and associated return) and air and water treatment media in a single connector. Separate couplings may be provided, or a four-port connector of virtually any other configuration may be provided.

FIG. 3 further illustrates that control unit 208 may have a housing 224 with attachment flanges 226. The attachment flanges allow the control unit 208 to be mounted at virtually any convenient location of the dental treatment center 100, and for example to the doctor delivery unit 112. Therefore, the dental treatment center 100 may consist of a pneumatic only treatment center adapted to include a system 200 by mounting the control unit 208 to the treatment center 100 and coupling the power cord 216 and media port 210 (compressed air and treatment media) to the control unit 208. Thereafter, an electric handpiece 122' may be coupled to the control unit via the quick connector 204 to complete the conversion of at least one handpiece station of the treatment center 100 to electric handpiece use.

While so far it has been described to configure a treatment center 100 with a single electric handpiece 122', the treatment center 100 may be configured to support more than one electric handpiece. In this regard, multiple systems 200 may be adapted to the dental treatment center 100. Alternatively, a control unit may be configured by providing connecting lines for multiple electric drive handpieces and, if necessary, multiple media inputs to support conversion of a dental treatment center for use with multiple electric drive handpieces.

Figure 4:
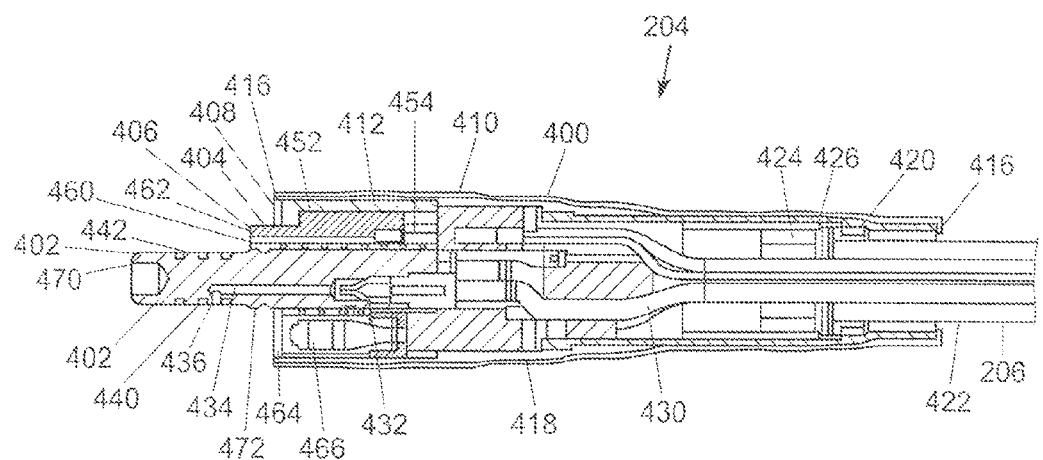
FIG. 4 is a cross section view of a handpiece connector of the system illustrated in FIG. 2.

With continued reference to FIGS. 2 and 3 and referring also to FIG. 4, the quick connector 204 includes a base portion 400 secured to the coupling line 206. The base portion 400 includes a multi-port nipple 402 and a retractable, spring biased electrical connector block 404 having an end portion 406 extending from an end surface 408 of the quick connector 204.

The connector 204 has a jacket or sleeve 410 made of a suitable durable material such as a medical grade metal including without limitation coated or plain stainless steel and an inner member 412 made of plastic or other suitable material. The inner member 410 may be a single molded part or an assembly of pieces. The jacket 410 defines a first aperture 414 and a second aperture 416 at opposing ends and a chamber 418 within. An end 420 of the coupling line 206 extends through the first aperture 414 and into the chamber 418. A jacket portion 422 of the coupling line 206, which may be multi-layer as shown, widens into a shoulder portion 424 within the chamber 418 and engages a bushing or shoulder portion 426 of the inner member 412 disposed within the chamber 418 adjacent the first aperture 414. Engagement of the shoulder portion 424 with the bushing portion 426 partially secures the coupling line 206 to the base portion 400. The coupling line 206 may be secured by friction, adhesive, combinations thereof or by any suitable device.

Figure 5:
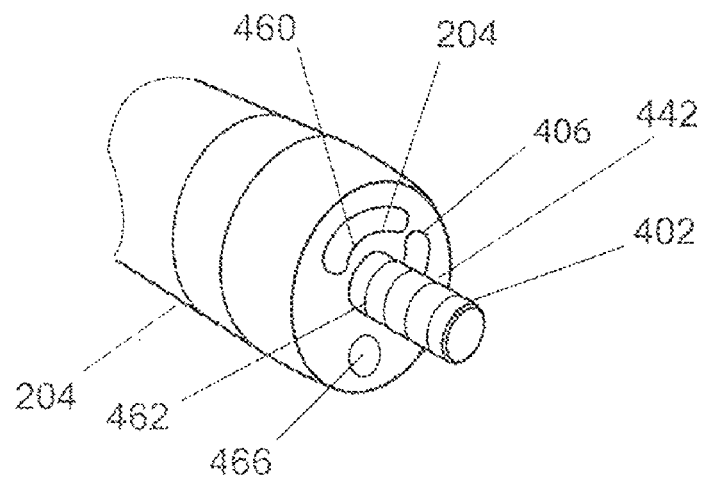
FIG. 5 is an end perspective view of the connector illustrated in FIG. 4.

Media lines, one illustrated as media line 430, corresponding to compressed source air, return air, treatment air and treatment water extend into the chamber. Each may couple via a check valve or other flow control device 432 to a via passage 434 leading to an aperture 436 formed in an outer surface 438 of the nipple 402. The nipple 402 is formed with a plurality of annular recesses 440 each receiving an o-ring 442 (depicted in FIG. 5) segmenting the nipple 402 into a plurality of segments 444. Each segment 444 corresponds to a media line and allows separate coupling of media to corresponding lines within the handpiece 122' (not depicted).

The electrical connecter block 404 is slideably received within a pocket 452 formed within the inner member 412. A spring 454 biases the electrical connector block 404 such that the first portion or protruding end 406 of the electrical connector block 404 may extend outwardly from the end surface 408 of the connector 204. The electrical connector block 404 is slideable within the pocket 452 so that the protruding end 406 of the connector block 404 may be pressed into the connecter 204 and not protrude from the end surface 408. Thus, the electrical connector block 404 is slidable between two positions. The first position is a position biased by the spring 454 at which the end portion 406 protrudes outwardly and beyond the end surface 408. In the second position, the electrical connector block 404 is pressed into the pocket 452 so that the protruding end 406 no longer protrudes from the end surface 408.

The protruding end 406, and in particular a surface 460 of the protruding end of the electrical connector is formed with a plurality of apertures 462 that extend into the electrical connector block 404. Each aperture 462 corresponds with a pin and socket type electrical connector. That is, disposed within each aperture 462 is a socket portion of a pin socket-type electrical connecter. Corresponding pin portions of the pin socket connectors are disposed within the handpiece 122'. Each socket portion is coupled to a conductor, a wire, a flexible conductor or other suitable connection, for example, which allows the electrical connector block 404 to move between its first and second positions. The conductors extend from the electrical connector block 404 into the line 206 and to control unit 208. Flange, tab, spade or other type connectors may be used in place of the pin socket-type connectors.

The end surface 408 is also formed with a lamp socket 464. A lamp 466 is received within the lamp socket 464 and is electrically coupled through the connector 204 to the base unit 208. Light emitted from the lamp 466 is coupled by a fiber optic disposed within the handpiece 122' to a lens that illuminates a work area during use of the handpiece 122'.

Figure 6:
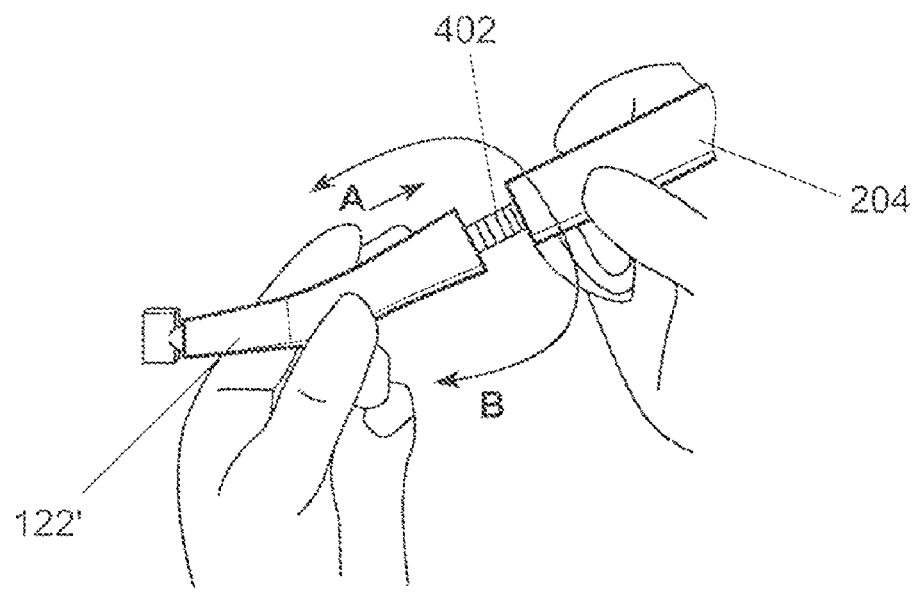
FIG. 6 is a schematic illustration of a handpiece attaching procedure.

The structure of the connector 204, the nipple 402 and the electrical connector block 404 facilitate coupling of a handpiece 122' to the connector 204. An end surface 470 of the nipple 402 may be chamfered to facilitate insertion into a corresponding socket formed in the handpiece 122'. The handpiece 122' and the connector 204 are simply pressed together as indicated by arrow "A" of FIGS. 2 and 6 until an end surface 128 of the handpiece 122' engages the end surface 408 of the connector 204. This action slides the electrical connector block 404 into the pocket 452. Then, the handpiece 122' is simply rotated, as indicated by the arrow "B" in FIGS. 2 and 6. When the electrical connector block 404 aligns within a socket (not depicted) formed in the handpiece 122', the spring 454 pushes the electrical connector block 404 into the socket. This action couples the pin socket-type connectors completing the electrical connection between the connector 204 and the handpiece 122' and hence completes the electrical connection between the control unit 208 and the handpiece 122'. Frictional engagement between the nipple 402 and the handpiece '116 socket, a detent or other structure may secure the handpiece 122' to the connector 204. For example, the nipple 402 may be formed with a ridge 472 to engage a clip, spring or other structure of the handpiece. Application of an axially directed force (arrow "A" in FIGS. 2 and 6) on the handpiece 122' separates the handpiece 122' from the connector 204. A more detailed description of the connector 204 is provided in the applicant's co-pending PCT/EP2007/009462 designating the United States of America, which is incorporate herein by reference.

Figure 7:
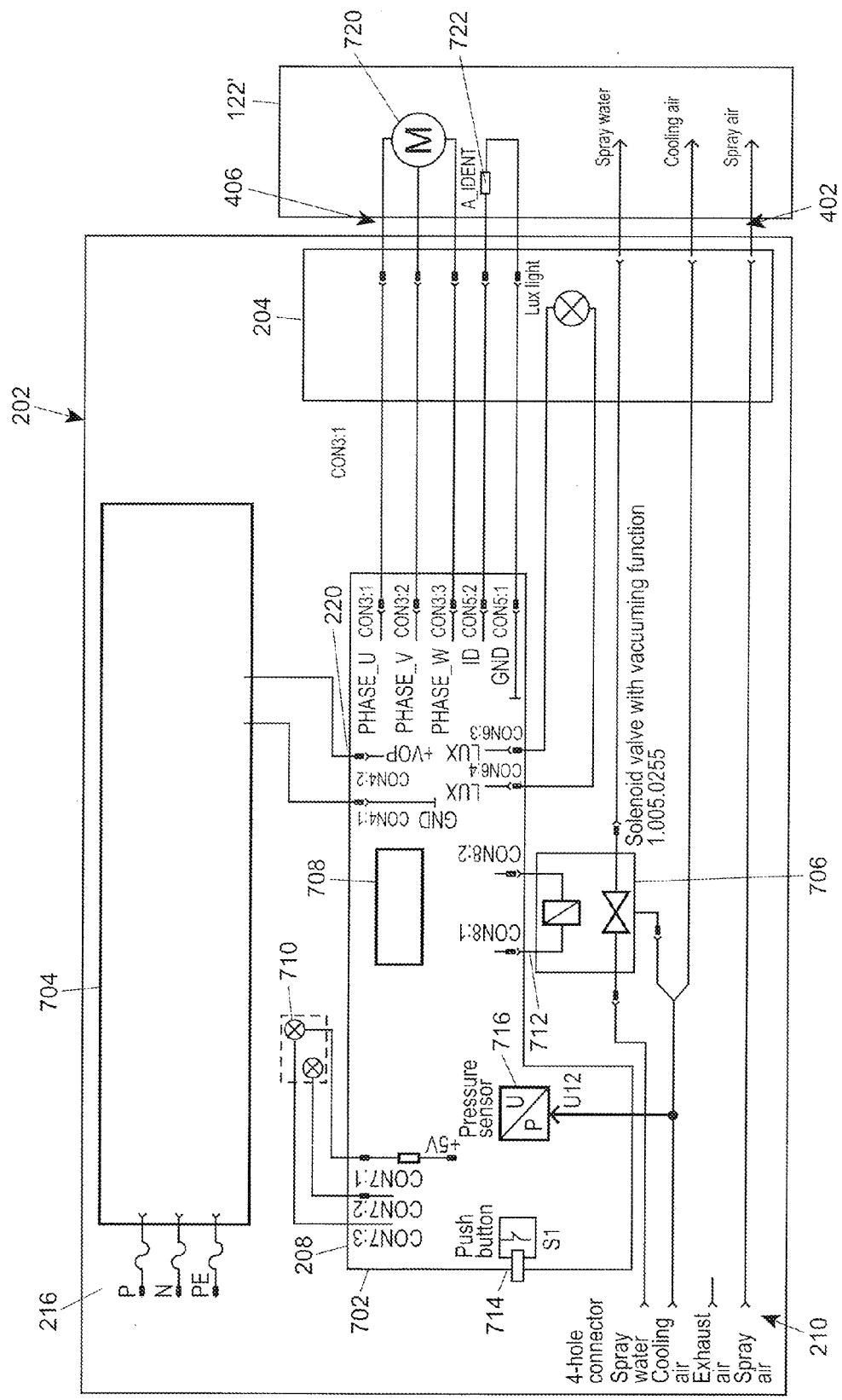
FIG. 7 is an electrical block diagram of the system illustrated in FIG. 2.

The system 200 is illustrated in block form in FIG. 7. The controller 208 includes control circuitry 702, power supply 704 and media control block 706. The control circuitry 702 may include a microprocessor, microcontroller, application specific integrated circuit (ASIC) chip and/or dedicated circuitry, memory 708 and other circuitry for affecting operation of the controller 208 as described herein. The control circuitry 702 may communicate with the media control block 706 via conductors 712. The media lines connect to the controller 208 via the media connector, e.g., media connector 210, and extend to the connector 204 via the lines 206. The control circuitry 702 may couple to an indicator 710, such as LEDs and reset/test push button 714. The power cord 216 connects to the power supply 704, which provides power to the controller 208.

The control circuitry 702 incorporates a pressure transducer 716 coupled to the compressed air media line (indicated as "cooling air" in the figure as the compressed air source is further used for cooling purposes) via the media port 210. The pressure transducer 716 provides a pressure signal to the control circuitry 702 indicative of the instantaneous pressure of the compressed air. The control circuitry 702 is adapted to determine from the pressure signal the pressure of the compressed air including a maximum pressure of the compressed air to store that value in the memory 708. As described below, the control circuitry 702 is capable of providing an automatic calibration process to determine a characteristic curve for controlling the handpiece 122' in response to modulation of the compressed air source via the pedal 116. The orientation of the handpiece 122', shown on the left side of the controller 208 in FIG. 2 and on the right side of the controller 208 in FIG. 7, is merely for convenience of the figures and the description. Either configuration may be employed in implementing the invention.

The media control block is further capable of communicating media to the handpiece 122' for cooling purposes. Additionally, the media control block is operable also to provide treatment media, such as air or water, to the work site.

The handpiece 122' incorporates a motor 720, driven by an electric signal provided to it by the control circuitry 702. The handpiece 122' may also include identification circuitry 722. The identification circuitry 722 may be interrogated by the control circuitry 702 to identify the handpiece 122' as being compatible with the system 200. The identification circuitry 722 may also identify the type of handpiece 122' and potentially a calibration profile saved within the memory 708 corresponding to it. The identification circuitry 722 simply may be a resistor the value of which is measured by the control circuitry 702.

One of the operating functions of the controller 208 is an automatic self-calibration upon initiating use and continuous recalibration during use. Calibration of the system 200 ensures the highest operating speed of the handpiece can be attained. Continuous recalibration ensures that the highest operating speed can be consistently obtained. Providing with widest operating speed range provides enhanced sensitivity especially at the highest and lowest operating speeds.

Figure 8:
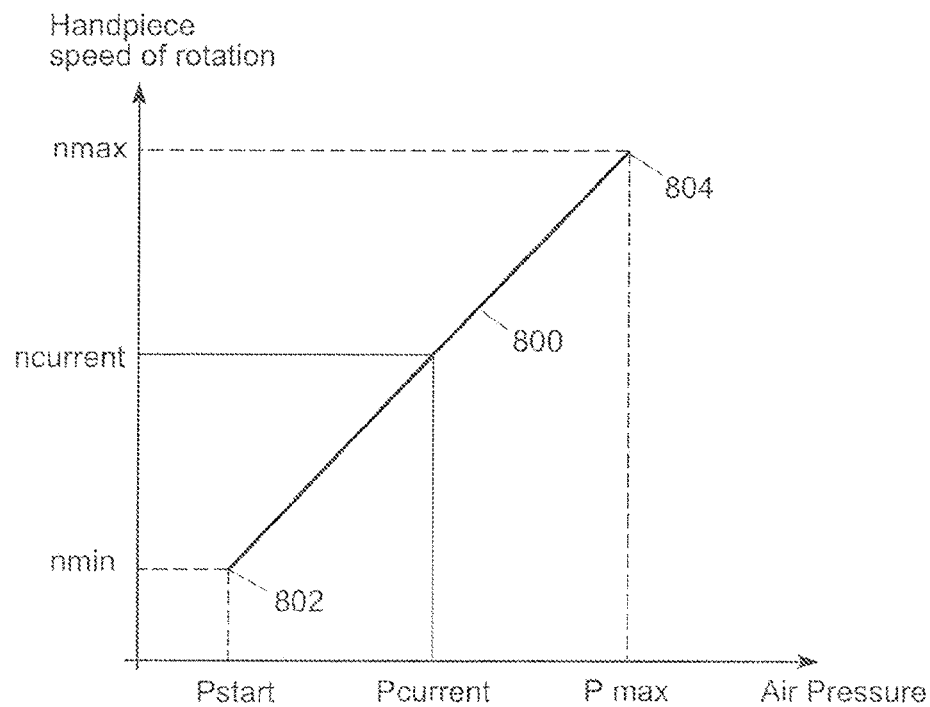
FIGS. 8 and 9 are graphs illustrating a calibration and adaptation of a control unit for a system for driving an electric handpiece in response to a pneumatic control signal in accordance with embodiments of the invention.

FIG. 8 shows a transfer function 800 in accordance with which the input pressure is converted into a speed of rotation of the handpiece 122. This transfer function 800 is based on two reference points 802 and 804 defining a generally straight-line response characteristic in the illustrated embodiment. Alternate response characteristics, such as arcs of various curvature, may be employed.

An input pressure value $p_{start}$ is associated with a minimal speed of rotation $n_{min}$. Only when this input pressure value $p_{start}$ is exceeded is thus the electric motor started and operated with the minimal speed of rotation $n_{min}$. With increase of pressure there is then effected a corresponding increase of the speed of rotation, until the maximum pressure $p_{max}$ is achieved, which corresponds to a maximum speed of rotation $n_{max}$ for the motor. Thus based on this transfer function 800 during running operation an instant pressure value $p_{current}$ can at any time be associated with a corresponding speed of rotation $n_{current}$. Thus, an actuation of the pedal 116, via which the compressed air of the treatment center 100 can be varied, leads in the end to a change of speed of rotation of the handpiece 122'.

It is to be noted that the transfer function 800 is not restricted to the illustrated linear form. As an alternative to this it would also for example be conceivable to place between the two reference points 802 and 804 example a transfer function in form of an exponential curve, which would then open up the possibility of carrying out a finer setting in the lower range of speed of rotation.

Figure 9:
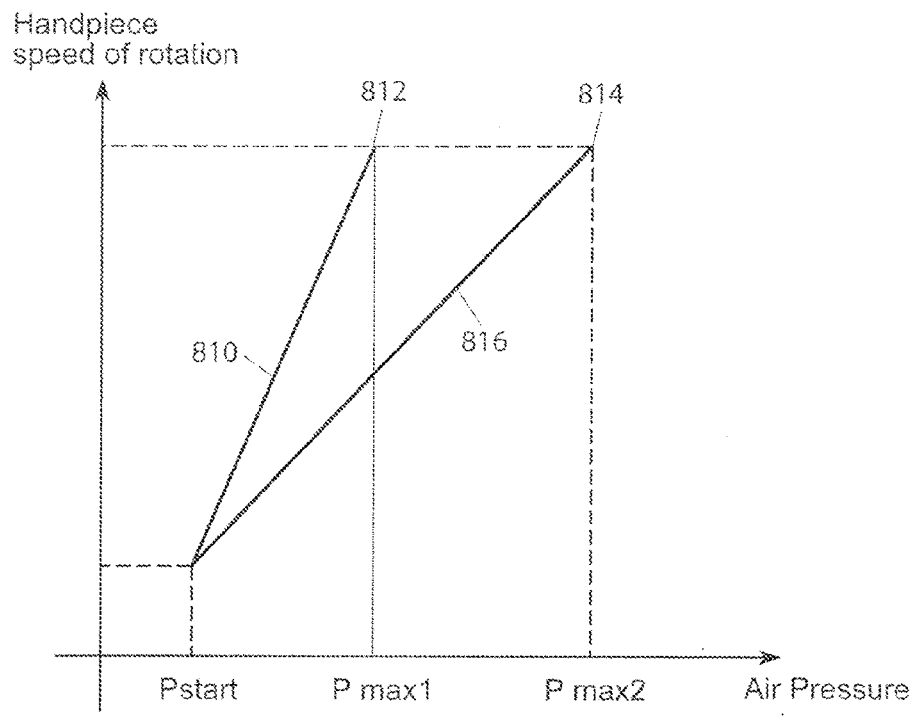

Independently of the form of the transfer function 800, for enhanced control and feel of operation of the handpiece 122' the transfer function 800 may be adapted to the current pressure conditions in an optimal manner. In other words, the upper reference point 804 should correspond as well as possible to the maximum pressure provided by the treatment center 100, in order to be able to fully exploit the control possibilities. Since however different dental-medical treatment centers provide compressed air in different pressure ranges, it is necessary to carry out a corresponding adaptation or a calibration for an optimal operation of the handpiece 122'. FIG. 9 illustrates a procedure to accomplish this in accordance with an embodiment of the invention.

In accordance with an embodiment of the invention, calibration is not limited to an initialization procedure. Instead, the control unit 208 of the system 200 is configured so that it determines continuously the input side air pressure and stores data relating to the same. In particular, the measured maximum pressure during running operation may be determined and stored. This maximum pressure is then taken into account for the formation of the upper reference point 804. A fixedly predetermined input pressure value $p_{start}$ may be used for the lower reference point 802. The transfer function 800 is then determined, by interpolation for example, between the two reference points.

FIG. 9 shows two cases. In a first case the system provides a maximum pressure $p_{max1}$. For this case, the transfer function 810 is automatically formed with the associated upper end-point 812. In the event, however, that in the course of the operation a higher maximum pressure $p_{max2}$ is determined, the upper reference point 814 is automatically adapted and correspondingly the transfer function 816 is defined.

An advantage of this procedure in accordance with an embodiment of the invention is that a transfer function optimally suitable for the corresponding system is generated automatically during running operation of the handpiece 122'. In the end, it is sufficient if the user of the system 200, upon first starting the handpiece 122', sets a maximum power with the aid of the pedal 116. Since this is normally carried out as a standard procedure, to briefly check the functioning of the system, there is no additional steps or procedures required for calibration.

The maximum pressure value $p_{max}$ determined by the controller 208 is further stored in the memory 708, which is preferably a non-volatile memory. Even after a temporary deactivation of the system 200, thus the correct transfer function is available automatically upon a restart. Pressing the test/reset button 714 deletes stored calibration data so that a new calibration is carried out when the system 200 is again used. Further it can be provided that the determined maximum pressure value is reduced slightly upon each restart of the handpiece 122' in order to automatically adapt the system to slightly changed pressure conditions. Of course, during operation, and in accordance with embodiments of the invention, the maximum pressure and a corresponding transfer function are continuously determined.

Thus, through the procedure in accordance with embodiments of the invention, the use of the system 200 is simplified considerably while performance is enhanced. The requirement of a specific calibration process may be eliminated. Moreover, variations in the pressure of the input compressed air values does not automatically lead to changes in operating the possible operating speed of the handpiece 122', which can be optimally maintained. It is also conceivable not only to adjust the speed of the handpiece 122' but to also adjust the power, the torque and/or the material removal power of the tool operated by the medical instrument. Further, the system 200 may be configured to simply provide a digital control signal that could be provided to a device, which is then suitably used by the device. However, the system preferably directly assumes complete control, that is, to directly control a handpiece to the desired speed of rotation or power.

While specific embodiments are described, it should be understood that various aspects of the embodiments might be combined in a manner other than described herein. For example, the advantages of the connector 204 may be employed in dental treatment centers already configured for electric handpieces. Likewise, it is possible for a system 200 to take advantage of the automatic and continuous calibration process without also using the connector 204. Considering again FIG. 2, one may use a conversion kit for converting a pneumatic dental treatment center to electric. Such a kit would consist of the components of the system 200 and may further include one or more handpieces 122' in combination with suitable installation instructions.

While the present disclosure is susceptible to various modifications and alternative forms, certain embodiments are shown by way of example in the drawings and the herein described embodiments. It will be understood, however, that this disclosure is not intended to limit the invention to the particular forms described, but to the contrary, the invention is intended to cover all modifications, alternatives, and equivalents defined by the appended claims.

It should also be understood that, unless a term is expressly defined in this patent using the sentence "As used herein, the term _____ is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Unless a claim element is defined by reciting the word "means" and a function without the recital of any structure, it is not intended that the scope of any claim element be interpreted based on the application of 35 U.S.C. §112, sixth paragraph.

The invention claimed is:

1. A connector for coupling a handpiece to a dental treatment center, the connector comprising:
   a nipple having a plurality of segments defined by o-rings disposed within recesses formed in an outer surface of the nipple, an aperture formed in each segment extending from the outer surface to an interior of the nipple, and each aperture being coupled to a media line; and
   an electrical connector block slideable within a housing of the connector between a first position and a second position, where in the first position a portion of the electrical connector block extends from an end surface of the connector and in the second position the electrical connector block is disposed within the housing such that an end surface of the electrical connector block being even with the end surface of the connector.

2. The connector of claim 1, the electrical connector block comprising a pin portion or a socket portion of a pin and socket-type connector.

3. The connector of claim 1, the housing formed to include an aperture at one end thereof, a line received within the aperture, the line having a media line and an electrical conductor disposed therein.

4. The connector of claim 1, comprising a lamp being disposed within the housing.

5. The connector of claim 4, the lamp being disposed within a recess formed in the end surface.

* * * * *